(12) United States Patent
Mendelovici et al.

(10) Patent No.: US 6,525,201 B2
(45) Date of Patent: Feb. 25, 2003

(54) PROCESSES FOR PREPARING 6-HYDROXY-3,4-DIHYDROQUINOLINONE, CILOSTAZOL AND N-(4-METHOXYPHENYL)-3-CHLOROPROPIONAMIDE

(75) Inventors: Marioara Mendelovici, Rehovot (IL); Gideon Pilarsky, Holon (IL); Tamar Nidam, Yehud (IL); Ben-Zion Dolitzky, Petach Tikva (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 09/812,454

(22) Filed: Mar. 20, 2001

(65) Prior Publication Data

US 2002/0032333 A1 Mar. 14, 2002

Related U.S. Application Data

(60) Provisional application No. 60/190,588, filed on Mar. 20, 2000.

(51) Int. Cl.$^7$ ............................................. C07D 215/36

(52) U.S. Cl. ...................................................... 546/158

(58) Field of Search ........................................ 546/158

(56) References Cited

U.S. PATENT DOCUMENTS

| | | |
|---|---|---|
| 3,819,637 A | 6/1974 | Bell |
| 3,994,902 A | 11/1976 | Bell |
| 4,049,715 A | 9/1977 | Bell |
| 4,277,479 A | 7/1981 | Nishi et al. |
| 4,372,953 A | 2/1983 | Uchida et al. |
| 5,294,718 A | 3/1994 | Ujiie et al. |

FOREIGN PATENT DOCUMENTS

| | | | |
|---|---|---|---|
| JP | 0912605 | * | 3/1997 |
| JP | 10330262 | * | 12/1998 |

OTHER PUBLICATIONS

Ali A. Khalaf et al., "Modern Friedel–Crafts Chemistry XIII. Intra– and intermolecular cyclization of some carbonyl derivatives under Friedel–Crafts conditions" Bulletin de al Societe Chimique de France, (Jan./Feb. 1984) pp. 11–285—11–291.
Database Casreact on STN Chemical Abstracts, (Columbus OH, USA); No. 102:220723; W. Verboom et al., "The Madelung Synthesis of dihydro–1H–pyrrolo and tetrahydropyrido [1,2–a] indoles under mild conditions" Tetrahedron Lett. (1985).
Database Casreact on STN, Chemical Abstracts, (Columbus, OH, USA); No. 107:39554; W. Verboom et al., "Wynthesis of dihydro–1H–pyrrolo– and tetrahydropyrido [1,2–a] indoles via a modified Madelung", Tetrahedron (1986).
Database Casreact on STN, Chemical Abstracts, (Columbus, OH, USA), No. 113:23552; Christopher J. Easton et al., "Acyloxylation at the 4–position of azetidin–2–ones", J. Chem. Soc., Perkin Trans. 1 (1990).
Chem Abstracts Doc. No. 131:257448, Japanese Patent No. 11–269148, 1998.
Chem Abstracts Doc. No. 133:11150480k, Japanese Patent No. 2000–229944, 2000.
Chem Abstracts Doc. No. 127:34142; Japanese Patent No. 9–124605, 1995.

* cited by examiner

*Primary Examiner*—D. Margaret Seaman
(74) *Attorney, Agent, or Firm*—Kenyon & Kenyon

(57) ABSTRACT

A process for preparing 6-hydroxy-3,4-dihydroquinolinone by intramolecular Friedel-Crafts alkylation of N-(4-methoxyphenyl)-3-chloropropionamide in which an equivalent of N-(4-methoxyphenyl)-3-chloropropionamide is contacted with a Lewis acid in DMSO or a high boiling amide or amine at an elevated temperature of from about 150° C. to about 220° C. is provided. The process produces 6-HQ in high yield and a high state of purity such that it may be used in subsequent reactions toward the preparation of cilostazol without intermediate purification. A process for preparing cilostazol from 6-hydroxy-3,4-dihydroquinolinone prepared by the process and improved processes for preparing N-(4-methoxyphenyl)-3-chloropropionamide are also provided.

9 Claims, No Drawings

PROCESSES FOR PREPARING 6-HYDROXY-3,4-DIHYDROQUINOLINONE, CILOSTAZOL AND N-(4-METHOXYPHENYL)-3-CHLOROPROPIONAMIDE

CROSS-REFERENCE TO RELATED APPLICATION

This invention claims the benefit under 35 U.S.C. 1.119(e) of provisional application Serial No. 60/190,588, filed Mar. 20, 2000.

FIELD OF THE INVENTION

The invention relates to therapeutic quinolinone derivatives such as cilostazol and chemical intermediates useful for their preparation. The present invention also relates to 6-hydroxy-3,4-dihydroquinolinone, which is one such intermediate.

BACKGROUND OF THE INVENTION

The present invention pertains to 6-hydroxy-3,4-dihydroquinolinone ("6-HQ") of formula (I)

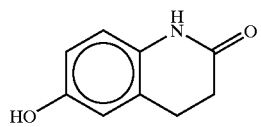

(I)

a known compound that is difficult to prepare on a large scale because of the sluggishness of the reaction by which it is prepared using conveniently accessible starting materials and because of the need to maintain a high reaction temperature throughout the reactor. 6-HQ has commercial importance as a key intermediate in the preparation of cilostazol.

Cilostazol (6-[4-(1-cyclohexyl-1H-tetrazol-5-yl) butoxy]-3,4-dihydro-2(1H)-quinolinone) is used to treat symptoms of intermittent claudication in patients suffering from symptoms of the disease, which include pain and cramping while walking due to reduced blood flow to the legs. Cilostazol has the chemical structure of formula (II).

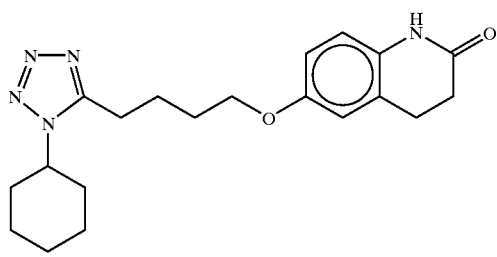

(II)

Cilostazol is described in U.S. Pat. No. 4,277,479, which teaches that it can be prepared by alkylating the phenol group of 6-HQ with a 1-cyclohexyl-5-(4-halobutyl)-tetrazole of formula (III).

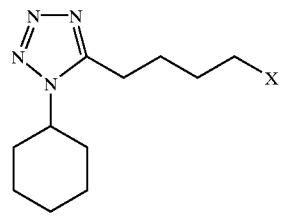

(III)

The first preparation of 6-HQ to appear in the U.S. patent literature is Example 11D of U.S. Pat. No. 3,819,637 (the '637 patent). In Example 11D, 6-HQ is prepared by cyclization of (p-methoxyphenyl)-3-chloropropionamide ("MCPA"). A blend of MCPA and $AlCl_3$ was heated with rapid stirring to produce a melt and then further heated to 150° C. and held at that temperature for half an hour. The melt was then poured into a slurry of cracked ice and hydrochloric acid to decompose the aluminum salts. 6-HQ was collected by filtration, washed with water and recrystallized from methanol. When these reaction conditions are scaled up, the high viscosity of the reaction medium causes temperature control problems. Cool regions form within the reactor and the 6-HQ and MCPA in those regions solidifies. Solidification hinders effective mixing of the reagents. Areas where high concentrations of $AlCl_3$ are caused by inadequate mixing can become "hot spots" where thermal decomposition of the reactant and product occur.

When we repeated the '637 process using 3 equivalents of $AlCl_3$, the reaction did not go to completion and we obtained the intermediate product N-(4-hydroxyphenyl)-3-chloropropionamide ("HPCA") in 28% yield. Though most of the HPCA could be removed by recrystallization from methanol as described in the '637 patent, 6-HQ could not be obtained substantially free of contamination with HPCA. Reducing the amount of $AlCl_3$ used in the reaction reduced the amount of HPCA but also reduced the overall yield of 6-HQ. The reaction time also increased; nevertheless, the rapidity of the melt process with either 2 or 3 equivalents of the catalyst is one of this method's merits.

The '637 process is a Friedel-Crafts alkylation. In contrast to Friedel-Crafts acylations, which have widespread utility, the usefulness of Friedel-Crafts alkylations is limited by a tendency toward over-alkylation of the aromatic participant, low aromatic regioselectivity and the tendency of carbocation intermediates to rearrange. One of the most important uses of Friedel-Crafts alkylation is ring closure, which is less affected by these limitations than intermolecular reactions are. There is an "intramolecular advantage" associated with generating the carbocation on the same molecule as the aromatic ring. The half-life of the carbocation is decreased by the high local concentration of the reacting partner, which minimizes rearrangement to a more stable secondary carbocation.

Despite the intramolecular advantage, cyclization of MCPA is sluggish because the substitution must occur at a position on the aromatic ring ortho to an electron withdrawing group. An amido group bonded to an aromatic ring through its nitrogen atom, like the amide group in MCPA, is ordinarily a weak activator of the ring toward electrophilic aromatic substitution. However, in the cyclization of MCPA, the amide carbonyl coordinates with $AlCl_3$. Coordination with $AlCl_3$ converts the amide group into an electron withdrawing substituent and deactivates the aromatic ring toward electrophilic substitution. The deactivating effect of a Lewis acid on aromatic ketones has been described in *Bull. Soc.*

Chim. Fr. 1984, 11, 285. In the '637 patent, high temperatures and the highest concentration attainable, i.e. a melt, were used to drive the cyclization onto the deactivated ring of MCPA.

The '637 patent also discloses in Example 11E a process for preparing the Friedel-Crafts starting material MCPA by adding 3-chloropropionyl chloride dropwise to a solution of p-anisidine in dry acetone.

Several investigators working in Japan have described modifications to the Friedel-Crafts reaction conditions of the '637 patent.

According to Chemical Abstracts Doc. No. 127:34142, Japanese Patent No. 9-124605 describes an improved process in which the MCPA and $AlCl_3$ are diluted with a liquid paraffin in mixture with either DMSO or an amide. Suitable amides in the JP '605 process include N,N-dimethylformamide ("DMF") and N,N-dimethylacetamide ("DMA"). A 76.9% yield of 6-HQ is reported after 20 h at 105° C. in a mixture of paraffin and DMA. Suitable paraffins are $C_7$–$C_4$ hydocarbons. For a large scale process, the lower molecular weight hydrocarbons are preferable for economic reasons. As an example, one liter of the $C_7$ hydrocarbon n-heptane costs less than a tenth as much of the $C_{12}$ hydrocarbon dodecane. In our hands and conducting the reaction in n-heptane and DMF at 100° C., the yield was lower than claimed in the JP '605 patent. The reaction also took longer but the purity of the product obtained after recrystallization from methanol and toluene was indeed improved over the '637 process. As is apparent from the Chemical Abstract, this process suffers from a slow reaction rate.

According to Chemical Abstracts Doc. No. 133:585428, Japanese Patent No. 2000-229944, describes the $AlCl_3$ catalyzed cyclization of MCPA in high boiling hydrocarbons like decahydronaphthalene and tetralin, and high boiling ethers like benzyl ethyl ether, isoamyl ether, diphenyl ether, diglyme and triglyme. Reaction of MCPA and $AlCl_3$ for 8 h in decahydronaphthalene at 150° C. gave 6-HQ in 90% yield. The JP '944 patent also discloses a preparation of MCPA from p-anisidine and 3-chloropropionyl chloride in DMF, DMA, DMSO and diphenyl.

According to Chemical Abstracts Doc. No. 131:257448, Japanese Patent No. 11-269148 describes the Friedel-Crafts intramolecular alkylation of MCPA in a mixture of a halobenzene and an amide or amine. The reaction may be performed at between 110° C. and 200° C. with 0.1 to 10 equivalents of amine. It is reported that 6-HQ was obtained in 78% yield after fifteen hours at 130° C. in a mixture o-dichlorobenzene and trioctylamine.

Aromatic solvents like benzene and tetralin are usually a poor solvent choice for conducting Friedel-Crafts alkylation reactions because the solvent, which is usually present in large excess, is susceptible to electrophilic attack. Halobenzenes like o-dichlorobenzene are somewhat deactivated towards electrophilic attack and, as mentioned, there is an intramolecular advantage favoring the Friedel-Crafts alkylation of MCPA. However, since the aromatic ring of MCPA is also deactivated, it was found that reaction with solvent was competitive with cyclization. The side products of reactions with solvent were detected as a complex pattern of peaks in the HPLC chromatogram of the product mixture that was absent from the chromatograms of the product mixtures from the melt and paraffin processes.

It would be desirable to have a process for making 6-HQ in a high level of purity, by a reaction that proceeds at a fast rate and with an improvement in the yield.

SUMMARY OF THE INVENTION

The present invention provides a process for preparing 6-hydroxy-3,4-dihydroquinolinone by intramolecular Friedel-Crafts alkylation of N-(4-methoxyphenyl)-3-chloropropionamide in which an equivalent of N-(4-methoxyphenyl)-3-chloropropionamide is contacted with about 3 to about 5 equivalents of a Lewis acid in DMSO or a high boiling amide or amine at an elevated temperature of from about 150° C. to about 220° C. A highly concentrated reaction mixture causes a fast reaction rate yet remains fluid throughout the reaction. The process produces 6-HQ in high yield and a high state of purity such that it may be used in subsequent reactions toward the preparation of cilostazol without intermediate purification. The present invention further provides a process for preparing cilostazol from 6-HQ prepared by the process. Improved processes for preparing N-(4-methoxyphenyl)-3-chloropropionamide are also provided.

DETAILED DESCRIPTION OF THE INVENTION

The present invention provides an improved process for preparing 6-hydroxy-3,4-dihydroquinolinone (I) from N-(4-methoxyphenyl)-3-chloropropionamide (IV). The transformation from starting material to product involves a ring closure and a demethylation of the phenol group as depicted in Scheme 1.

Scheme 1

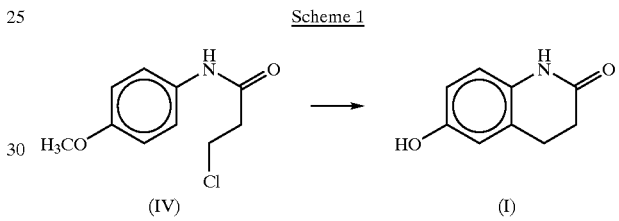

The present process is described using $AlCl_3$ as catalyst, although other Lewis acids known to be useful for promoting Friedel-Crafts reactions like $AlBr_3$, $FeCl_3$, $FeBr_3$, $SbF_5$, $TiCl_4$, $SnCl_4$ and $BF_3$ also may function effectively. The process uses from about 3 to about 5 molar equivalents of catalyst, preferably about 4 equivalents.

The reaction is conducted at high concentration in a diluent selected from the group consisting of DMSO, high boiling amines and high boiling N,N-disubstituted amides. Suitable amides and amines have boiling points in excess of 150° C. so that the reaction may be conducted at ambient pressure without significant loss of the diluent by evaporation. Some evaporation is acceptable and the use of a vapor condensor with the reactor is recommended. High boiling N,N-disubstituted amides and amines that may be used include those previously described in Chemical Abstract Doc. Nos. 127:34142 and 131:257448, i.e. N,N-dimethyl formamide ("DMF"), N,N-dimethylacetamide ("DMA") and octylamine and further include primary amines having $C_7$ and higher formula weight alkyl or aryl substituents, secondary amines having $C_4$ and higher formula weight alkyl or aryl substituents and tertiary amines having $C_4$ and higher formula weight alkyl or aryl substituents. The most preferred diluent is DMA.

The diluent is added to the MCPA in an amount of from about 1 to about 1.3 equivalents, preferably about 1.3 equivalents. A solution in DMA accordingly has a molal concentration (moles solute/kg. solvent) of MCPA of from about 8.8 to about 11.5 molal. When 4 equivalents of $AlCl_3$ is used as catalyst, this solution is from about 35.3 to about 45.9 molal in catalyst.

The reaction may be conducted at a temperature in the range of from about 150° C. to about 220° C., more preferably about 150° C. to about 160° C. Depending upon temperature, the reaction is substantially complete in 30 minutes to 2 hours. The reaction time is kept short by adding only an approximate molar equivalent of the diluent to the reaction mixture, which results in a highly concentrated reaction mixture.

The Friedel-Crafts cyclization obeys second order kinetics, consistent with a mechanism wherein the rate limiting step is the formation of the carbocation or MCPA-aluminum trichloride complex intermediate. The high rate of reaction and correspondingly short reaction time of the process are partly attributable to the high MCPA and $AlCl_3$ concentration in the reaction mixture. This aspect of the invention would be lost by the addition of a paraffin, halogenated aromatic or high boiling ether, and thus neither these substances nor any others are added to the reaction in amounts that would increase the reaction time beyond about 3 hours. Another important aspect of the invention is that despite the high concentration, it is less prone to solidification due to variations in temperature at different locations within the reactor than a melt is. The diluents of this invention maintain the fluidity of the reaction mixture even at high concentration. As discussed below, a reaction mixture in DMA slurries as the reaction nears completion, but the slurry is easily stirred and does not cause hot spots.

The process is further illustrated with an illustrative step-wise description of the process in which the catalyst is $AlCl_3$ and the solvent is DMA. The process may be performed in a reactor equipped with a heater, paddle stirrer, powder funnel, thermometer and vapor condensor. The reactor is charged with MCPA and 1.3 equivalents of DMA. The powder funnel is charged with 4 equivalents of $AlCl_3$. $AlCl_3$ is added slowly while stirring the cloudy mixture and monitoring the thermometer or reflux rate for excessive exotherm. Preferably, the temperature should not be allowed to exceed about 160° C. during the addition. If a rapid exotherm occurs, control of the temperature may be regained by shutting off the flow of $AlCl_3$ and allowing reflux to cool the reactor or by cooling the reactor externally. After completing the addition, progress of the reaction may be monitored by TLC (eluent: (12:8:2:2) MEK:$CHCl_3$:$CH_2Cl_2$:IPA; $R_f$(6-HQ)=0.5). One indication that the reaction is nearing completion is that the mixture which originally was a slightly cloudy solution becomes a slurry. The slurry is easily stirred and does not contribute to hot spot formation in the reactor. The reaction typically takes another 30 minutes to 2 hours to go to completion after the addition of $AlCl_3$ is complete.

The reaction may be quenched by slowly pouring the reaction mixture into aqueous or alcohol solution in a well ventilated area and then decomposing the aluminum salts with sodium borohydride and recovering 6-HQ by filtration. The aluminum salts also can be decomposed with hydrochloric acid.

The 6-HQ obtained by practicing the foregoing process may be used to prepare cilostazol by the novel method disclosed in U.S. patent application Ser. No. 09/929,683 which is hereby incorporated by reference in its entirety. The 6-HQ obtained by practicing the foregoing process also may be used to prepare cilostazol by other methods, such as the method described in U.S. Pat. No. 4,277,479, which is herein incorporated by reference for its teaching of the preparation of 3,4-dihydroquinolinone derivatives from 6-HQ. According to the '479 patent's method, 6-HQ is dissolved in ethanol containing DBU. 1-Cyclohexyl-5-(4-iodobutyl)-tetrazole is added dropwise to the refluxing solution over ninety minutes and the reaction mixture is refluxed for another 5 hours. The mixture is then concentrated and taken up in chloroform which is washed with dilute NaOH, dilute HCl and water. The organic phase is then dried over sodium sulfate and evaporated. The residue is recrystallized from an ethanol and water mixture to give cilostazol having a melting point of 148–150.5° C.

The MCPA (IV) starting material for preparing 6-HQ may be prepared by improved acylation processes which produce MCPA in high yield and high purity which is suitable for use to prepare 6-HQ without chromatographic purification. Comparision of the results in Table 2 of the Examples shows that the following processes produce MCPA with purity comparable to the product obtained from the process of the '637 patent but in a higher yield. The transformation from starting materials to product involves an acylation of p-anisidine with 3-chloropropionyl chloride as depicted in Scheme 2.

Scheme 2

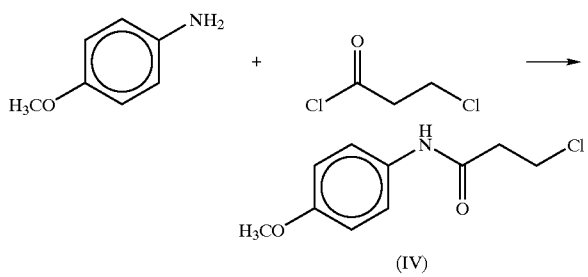

(IV)

The improvement over known processes for acylating p-anisidine with 3-chloropropionyl chloride resides in the base/solvent combinations used in the processes and the reaction conditions, particularly temperature, which provide the optimum yields and purity with the particular solvent/base combination.

In the most preferred of these processes, p-anisidine is dissolved in a sufficient amount of toluene to produce an approximately 3 to 5 M solution, more preferably about 4 M solution. Between 1 and 2 equivalents, more preferably about 1.5 equivalents, of sodium bicarbonate ("$NaHCO_3$") are suspended in the p-anisidine solution and the resulting suspension is stirred while an approximately equivalent amount 3-chloropropionyl chloride (i.e. 1–1.2 eq.) is added dropwise to the stirred suspension. The addition may be conducted at reduced or ambient temperature and the temperature may be allowed to rise, but should not be allowed to exceed 70° C. After completing the addition, the temperature of the reaction is maintained at between room temperature and the reflux temperature of toluene (111° C.), most preferably about 60° C., for a time sufficient for the reaction to be complete. Progress of the reaction may be monitored by TLC using the method described in Example 2a. After the reaction is complete, the reaction mixture is quenched with water or aqueous mineral acid and MCPA is isolated from the resulting suspension by filtration, decantation and the like, preferably filtration. The MCPA is then washed with water, toluene, or other nonviscous liquid in which the MCPA is not substantially soluble. The washed solid is then dried.

In another acylation process, N,N-dimethylformamide ("DMF") fulfills the function of solvent and acid scavenger. p-Anisidine is dissolved in an amount of DMF to produce an approximately 2 to 3 M solution, more preferably about 2.7 M solution of p-anisidine in DMF. The from 1 to 1.2 equivalents of 3-chloropropionyl chloride are added to the solution. The reaction proceeds smoothly to completion in about 4 hours without external heating. MCPA may then be isolated from the reaction mixture by the method described with reference to the toluene/NaHCO$_3$ process.

In an alternative acylation process which gives MCPA in high purity, albeit in lower yield than the toluene/NaHCO$_3$ process, p-anisidine is dissolved in sufficient methyl ethyl ketone ("MEK") to give an approximately 3 to 5 M solution, preferably about 4 M. Between 0.9 and 1.2 equivalents of triethyl amine ("Et$_3$N") is added to the solution as acid scavenger followed by slow addition of between 0.9 and 1.2 equivalents of 3-chloropropionyl chloride. As previously described with reference to the toluene/NaHCO$_3$ process, the addition may be conducted at reduced or ambient temperature and the temperature may be allowed to rise, but should not be allowed to exceed 70° C. After completing the addition, the solution is refluxed (80° C.) for a time sufficient to complete the reaction which may be determined by TLC using the method described in Example 2a. MCPA is then isolated from the reaction mixture as described with reference to the toluene/NaHCO$_3$ process.

In yet another acylation process, p-anisidine is dissolved in sufficient dichloromethane to produce an approximately 2 to 4 M solution, more preferably about 3 M solution of p-anisidine. Approximately one equivalent of aqueous sodium hydroxide and approximately one equivalent of 3-chloropropionyl chloride are then added slowly and simultaneously to the solution so as to maintain an approximately neutral pH in the organic phase. The addition is preferably performed at controlled low temperature of 0° C. or less. The reaction may be quenched and the MCPA product may be isolated by the methods described with reference to the toluene/NaCO$_3$ process.

The following specific examples are provided to further illustrate the practice of the present invention. It is not intended that the invention be limited in any way by these examples which are provided for the purpose of illustration only.

EXAMPLES

General p-Anisidine of 99% purity and 3-chloropropionyl chloride of 98% purity were used as received from Acros Organics. Other reagents and solvents were also used as received.

High performance liquid chromatography ("HPLC") was performed using the following conditions: column and packing Zorbax®RX-C$_8$250×4.6 mm, 5 μm; UV detection: λ=254 nm; flow rate: 1 ml/min linear gradient; gradient elution: solvent A=0.02 M trisodium citrate dihydrate in water adjusted to pH 5.3 with 0.07 M citric acid (~100 ml), solvent B=acetonitrile. The gradient program is shown below.

| Time (min) | Eluent A (%) | Eluent B (%) |
|---|---|---|
| 0 | 85 | 15 |
| 40 | 50 | 50 |

Example 1

Preparation of 6-hydroxy-3.4-dihydroquinolinone

N-(4-methoxyphenyl)-3-chloropropionamide (300 g, 1.4 mol.) and N,N-dimethylacetamide (165 ml, d=0.937, 1.3 eq.) were added to a three-necked, three-liter flask. Trichloroaluminum (760 g, 4 eq.) was slowly added over two hours. An exotherm raised the temperature of the mixture from about 25° C. to 140° C. over the course of the addition. The reaction mixture was a slightly cloudy colorless solution. The solution was stirred and held at 150–160° C. for two hours. At the end of the two hours the reaction mixture had become a stirrable slurry. The mixture was then cooled to ambient temperature and quenched by pouring into water (5.5 L) in a fume hood with good circulation and a trap between the inlet and the exhaust to capture evolved HCl gas. Next, sodium borohydride (30 g) was added, which caused the mixture color to turn from gray to white. The mixture was then cooled to ambient temperature and filtered. The collected solids were washed with water (2 L) and dried overnight in a vacuum-oven at 60° C. to give 6-hydroxy-3,4-dihydroquinolinone (212.8 g, 92.9%) in 99.2% purity based on HPLC analysis.

As shown in Table 1, entries 2–4, when 1.3 equivalents of DMA was used, the reaction was reproducible, giving 6-HQ in an average yield of 91.6% and an average purity of 98.9%. As also shown in Table 1, entry 1, reduction of the DMA content to 1 equivalent caused a reduction in yield and increase in HCPA content of the product but nevertheless produced a superior product compared to the methods known to the art. Cyclization of MCPA in the highly concentrated solutions according to the present invention produces 6-HQ in improved yield and higher purity than does cyclization in a melt (compare Table 1 entries 1–4 with entries 5 and 6). These improvements are achieved without the significant increase in reaction time observed when the reaction is conducted in paraffin or a halobenzene (compare Table 1, entries 1–4 with entries 7 and 8).

TABLE 1

| | | Reaction Medium | | | | Purity Analysis Compound (% area) | | | | | |
|---|---|---|---|---|---|---|---|---|---|---|---|
| Entry | AlCl$_3$ (eq.) | 1st Diluent (eq.) Diluent | 2nd | Temp. (° C.) | Time (h) | 6-HQ % Yield | 6-HQ | HCPA | N—CH$_3$-6-HQ[a] | MCPA | 6-MQ[b] |
| 1 | 4 | DMA (1) | — | 150 | 2.5 | 83.6 | 97.9 | 1 | 0.07 | | |
| 2 | 4 | DMA (1.3) | — | 150–160 | 2 | 94.4 | 98.8 | 0 | 0.2 | 0.12 | 0.11 |
| 3 | 4 | DMA (1.3) | — | 150–160 | 2 | 92.9 | 99.2 | 0.06 | 0.06 | 0.23 | |
| 4 | 4 | DMA (1.3) | — | 150–160 | 2 | 87.5 | 98.7 | 0.05 | 0.15 | 0.42 | |
| 5 (comparative[c]) | 3 | — | — | 160 | 0.5 | 62.3 (60)[d] | 70.6 (94.9)[d] | 28.3 (4.25)[d] | (0.14)[d] | | |

TABLE 1-continued

| Entry | AlCl₃ (eq.) | Reaction Medium 1st Diluent (eq.) Diluent | 2nd | Temp. (° C.) | Time (h) | 6-HQ % Yield | Purity Analysis Compound (% area) 6-HQ | HCPA | N—CH₃-6-HQ[a] | MCPA | 6-MQ[b] |
|---|---|---|---|---|---|---|---|---|---|---|---|
| 6 | 2 | — | — | 150 | 2 | 80.8 | 98.7 | | | | 0.09 |
| 7 (comparative[e]) | 2 | DMF (1) | o-dichlorobenzene | 130 | 6 | 79.2 | 73.7[f] | 0.03 | | | |
| 8 (comparative[g]) | 3.5 | DMF (1.1) | n-heptane | 100 | 26 | (60)[h] | (96.4)[h] | (1.7)[h] | (0.12)[h] | (0.12)[h] | |

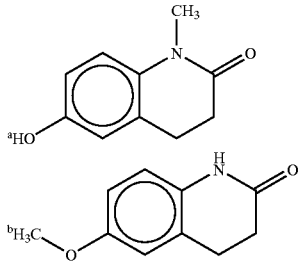

[a]HO- (structure shown)
[b]H₃C-O- (structure shown)
[c]U.S. Pat. No. 3,819,637
[d]After recrystallization from methanol
[e]JP 11-269149
[f]26.3% area complex peak pattern attributed to side reactions with solvent
[g]JP 9-124605
[h]After recrystallization from methanol/toluene

Example 2a

Preparation of N-(4-methoxyphenyl)-3-chloropropionamide in Toluene/NaHCO₃ p-Anisidine (200 g) and NaHCO₃ (205 g) were added to toluene (400 ml) in a three-liter, three-necked flask. A solution of 3-chloropropionyl chloride (207.5 g) in toluene (400 ml) was added drop-wise over an hour and a half to the mixture and the temperature of the reaction mixture was allowed to rise to 50° C. After completing the addition, the reaction mixture was heated to 60° C. for about one hour. The reaction was monitored by TLC (eluent: (12:8:2:2) MEK:CHCl₃:CH₂Cl₂:IPA). The mixture was cooled to ambient temperature. Concentrated hydrochloric acid (100 ml) was diluted 10 to 1 with water and added to the mixture over thirty minutes at ambient temperature. The mixture was filtered and the collected salts were washed with water (500 ml), and then toluene (250ml). The resulting product was dried overnight at 60° C. The dried product was N-(4-methoxyphenyl)-3-chloropropionamide (334 g, 96.2%) in 99.65% purity by HPLC analysis.

Example 2b

Preparation of N-(4-methoxyphenyl)-3-chloropropionamide in MEK/Et₃N

A three-necked flask was charged with p-Anisidine (50 g), Et₃N (40.43 g) and methyl ethyl ketone (100 ml). The resulting slurry was cooled to 10C and 3-chloropropionyl chloride (50.74 g) was slowly added. The temperature was allowed to rise to 60° C. during the addition. The mixture was then refluxed for 1 hour and cooled to 50° C. The solids were collected by filtration, washed with water, and dried at 50° C. to constant weight to give N-(4-methoxyphenyl)-3-chloropropionamide (56.42 g, 86.8%).

Example 2c

Preparation of N-(4-methoxyphenyl)-3-chloropropionamide in DMF p-Anisidine (10 g) was dissolved in DMF (30ml ). 3-Chloropropionyl chloride (10.12 g) was added at ambient temperature and the solution was stirred for about four hours. The reaction mixture was quenched with water. The solid product was isolated by filtration and dried under vacuum at 60° C. to give MCPA (13.05 g, 76.7%) in 99.5% purity based upon HPLC analysis.

Example 2d

Preparation of N-(4-methoxyphenyl)-3-chloropropionamide in CH₂Cl₂/NaOH p-Anisidine (12.3 g) was dissolved in CH₂Cl₂ (30 ml) and the solution was cooled to 5° C. Aqueous NaOH (6.6 g in 13 ml water) and 3-chloro-propionyl-chloride (19.05 g) were simultaneously added to the above solution over 40 minutes. The two phase mixture was stirred at 5° C. for another 30 min. Water (250 ml) and concentrated HCl (3 ml) were then added . The product was isolated by filtration, washed with water and dried to a constant weight to give N-(4-methoxyphenyl)-3-chloropropionamide (29.7 g, 94.6 %) in 99.3% purity by HPLC analysis.

TABLE 2

| Equivalents of p-Anisidine | Solvent | Base | Temp. (° C.) | % Yield | % Purity |
|---|---|---|---|---|---|
| (comparative[a]) 2 | acetone | — | reflux | 88 | 99.5 |
| 1 | MEK | Et₃N | reflux | 86.8 | n.d.[b] |
| 1.2 | DMF | — | r.t. | 76.7 | 99.5 |
| 1 | CH₂Cl₂ | NaOH | -5 | 94.5 | 99.3 |
| 1 | Toluene | NaHCO₃ | 60 | 94.2 | 99.5 |
| 1 | Toluene | NaHCO₃ | 60 | 96.5 | 99.6 |
| 1 | Toluene | NaHCO₃ | 60 | 96.2 | 99.7 |

[a]U.S. Pat. No. 3,819,637,
[b]Not determined

As can be seen from the results summarized in Table 2, acylation of p-anisidine with 3-chloropropionyl chloride in toluene with NaHCO₃ as acid scavenger consistently gave high yields and high purity of MCPA without chromatographic purification or recrystallization. Conduct of the reaction in MEK, DMF and $CH_2Cl_2$ according to Examples 2b–d provides alternative processes for making MCPA with their own distinct advantages such as operating at reduced or ambient temperature.

Having thus described the present invention with reference to certain preferred embodiments and illustrated it with examples, one skilled in the art will recognize variations and substitutions in the methods as described and exemplified which do not depart from the spirit and scope of the invention as defined by the claims which follow.

We claim:

1. A process for preparing 6-hydroxy-3,4-dihydroquinolinone by cyclization of N-(4-methoxyphenyl)-3-chloropropionamide comprising the steps of:
   a) contacting an equivalent of N-(4-methoxyphenyl)-3-chloropropionamide with about 3 to about 5 equivalents of a Lewis acid catalyst in a paraffin-free diluent selected from the group consisting of dimethyl sulfoxide, N,N-disubstituted amides and arnines having a boiling point of 150° C. or above, the diluent being present in an amount of from about 1 to about 1.3 equivalents with respect to the N-(4-methoxyphenyl) 3-chloropropionamide, at an elevated temperature of from about 150° C. to about 220° C. for a period of time sufficient to cause substantially all of the N44-methoxyphenyl)-3-chloropropionamide to cyclize and demethylate resulting in the formation of a Lewis acid salt of 6-hydroxy-3,4-dihydroquinolinone, and thereafter,
   b) decomposing the Lewis acid salt of 6-hydroxy-3,4-dihydroquinolinone, and
   c) isolating 6-hydroxy-3,4-dihydroquinolinone.

2. The process of claim 1 wherein the Lewis acid is selected from the group consisting of $AlCl_3$, $AlBr_3$, $FeCl_3$, $FeBr_3$, $SbF_5$, $TiCl_4$, $SnCl_4$ and $BF_3$.

3. The process of claim 2 wherein the Lewis acid is $AlCl_3$.

4. The process of claim 3 wherein the N-(4-methoxyphenyl)-3-chloropropionamide is contacted with about 4 equivalents of $AlCl_3$.

5. The process of claim 1 wherein the time sufficient to cause substantially all of the N-(4-methoxyphenyl)-3-chloropropionamide to cyclize is three hours or less.

6. The process of claim 1 wherein the N-(4-methoxyphenyl)-3-chloropropionamide and Lewis acid are contacted at an elevated temperature of from about 150° C. to about 160° C.

7. The process of claim 1 and thereafter converting the 6-hydroxy-3,4-dihydroquinolinone to 6-[4-(1-cyclohexyl-1H-tetrazol-5-yl)butoxy]-3,4-dihydro-2(1H)-quinolinone or a pharmaceutically acceptable salt thereof.

8. The process of claim 7 wherein the conversion of 6-hydroxy-3,4-dihydroquinolinone to 6-[4-(1-cyclohexyl-1H-tetrazol-5-yl)butoxy]-3,4-dihydro-2(1H)-quinolinone or a pharmaceutically acceptable salt thereof is by reaction of 6-hydroxy-3,4-dihydroquinolinone with a 1-cyclohexyl-5-(4-halobutyl)-tetrazole in the presence of an organic or inorganic base.

9. A process for preparing 6-hydroxy-3,4-dihydroquinolinone by cyclization of N-(4-methoxyphenyl)-3-chloropropionamide comprising the steps of:
   a) contacting an equivalent of N-(4-methoxyphenyl)-3-chloropropionamide with about 3 to about 5 equivalents of a Lewis acid catalyst in a reaction medium consisting essentially of a diluent selected from the group consisting of dimethyl sulfoxide, N,N-disubstituted amides and amines having a boiling point of 150° C. or above, the diluent being present in an amount of from about 1 to about 1.3 equivalents with respect to the N-(4-methoxyphenyl)-3-chloropropionamide, at an elevated temperature of from about 150° C. to about 220° C. for a period of time sufficient to cause substantially all of the N-(4-methoxyphenyl)-3-chloropropionamide to cyclize and demethylate resulting in the formation of a Lewis acid salt of 6-hydroxy-3,4-dihydroquinolinone, and thereafter,
   b) decomposing the Lewis acid salt of 6-hydroxy-3,4-dihydroquinolinone, and
   c) isolating 6-hydroxy-3,4-dihydroquinolinone.

* * * * *